United States Patent [19]

Shimada et al.

[11] Patent Number: 4,743,689
[45] Date of Patent: May 10, 1988

[54] ANTIBIOTIC DERIVATIVE OF ADENINE

[75] Inventors: Nobuyoshi Shimada, Tokyo; Shigeru Hasegawa, Saitama; Takashi Harada; Takayuki Tomizawa, both of Tokyo; Akio Fujii, Kanagawa, all of Japan

[73] Assignee: Nippon Kayaku Kabushiki Kaisha, Tokyo, Japan

[21] Appl. No.: 796,114

[22] Filed: Nov. 8, 1985

[30] Foreign Application Priority Data

Nov. 20, 1984 [JP] Japan ................. 59-243172

[51] Int. Cl.$^4$ ............... C07D 473/34; A61K 31/52
[52] U.S. Cl. ................................ 544/277; 435/88
[58] Field of Search ............... 544/276, 277; 514/263

[56] References Cited

U.S. PATENT DOCUMENTS 4,241,063 12/1980 Naito et al. ................. 424/253
4,321,376 3/1982 Otani et al. ................. 544/277
4,543,255 9/1985 Shealy et al. ................ 544/277

Primary Examiner—Nicholas S. Rizzo
Attorney, Agent, or Firm—Henry C. Nields

[57] ABSTRACT

This invention relates to a novel antibiotic NK84-0218 of the formula:

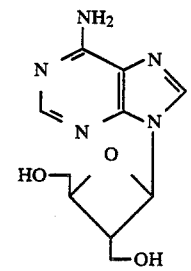

which exhibits antibacterial, antiviral and antineoplastic activities and is expected as a pharmaceutical as well as a process for the production of the same.

1 Claim, 3 Drawing Sheets

ANTIBIOTIC DERIVATIVE OF ADENINE

BACKGROUND OF THE INVENTION

Antineoplastic adenine antibiotics such as cordycepin(3'-deoxyadenosine; cf. Bio-chim. Biophys. Acta, 117, 482 (1966)) have been known. Up to now, no compound wherein an oxetane ring is attached to adenine has been reported.

By the way, with the appearance of resistant bacteria it is always required to develop novel antibiotics. Further there are various kinds of viral diseases and malignant tumors, which also makes novel antiviral and antineoplastic active substances necessary.

SUMMARY OF THE INVENTION

Under these circumstances, we have examined various metabolites of microorganisms and consequently found that a strain belonging to the genus Bacillus produces a novel antibiotic NK84-0218 of the formula (I):

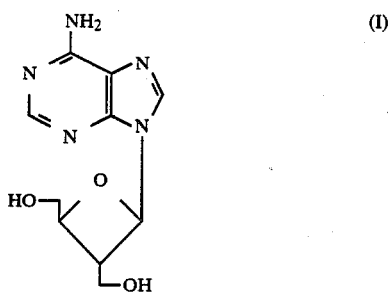

which exhibits antibacterial, antiviral and antineoplastic activities.

The present invention has been completed based on the above finding.

DETAILED DESCRIPTION OF THE INVENTION

Figure 1:
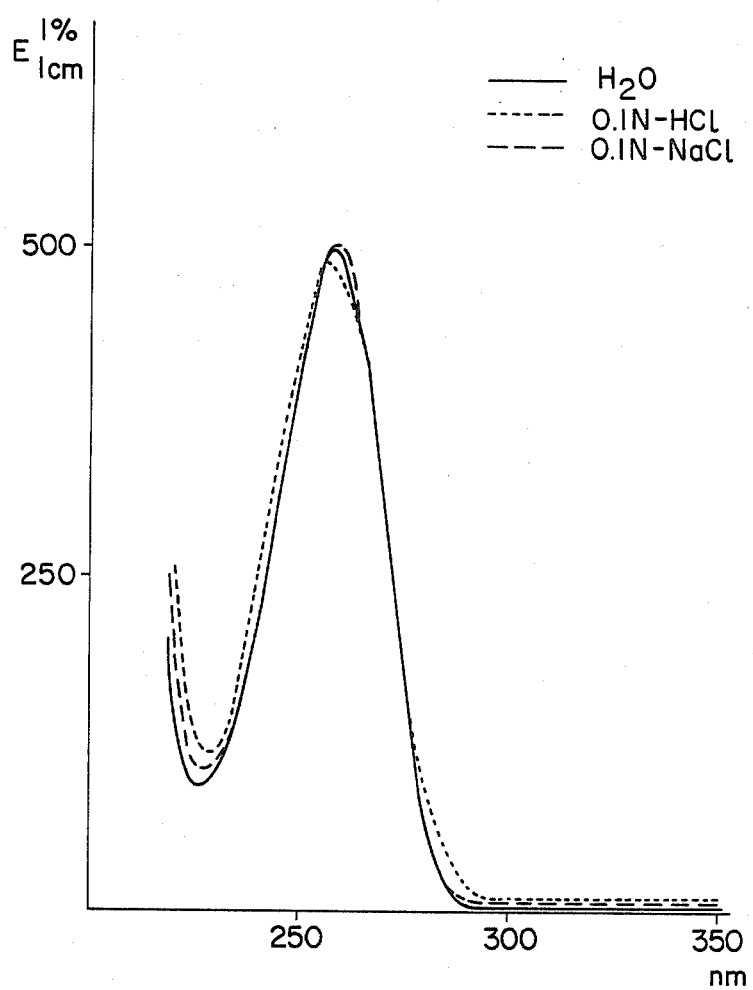
FIG. 1 shows ultraviolet absorption spectra of NK84-0218.

The novel antibiotic NK84-0218 described above can be obtained by culturing an NK84-0218-producing bacterium belonging to the genus Bacillus to thereby allow the microorganism to accumulate the antibiotic NK84-0218 and collecting the antibiotic NK84-0218 from the medium. A typical example of the NK84-0218-producing bacterium is Bacillus NK84-0218 (FERM BP-919, deposited at the Fermentation Research Institute Agency of Industrial Science and Technology, 1-3, Higashi 1-chome Yatabe-machi Tsukuba-gun Ibaraki-ken 305, Japan; hereinafter referred to as NK-84-0218 strain) which was isolated from soil in the Director Research Laboratories of Nippon Kayaku Co., Ltd. in December, 1983.

Now mycological properties of the NK84-0218 strain will be described.

1. Morphological properties
   (1)
   Cell form: rod.
   Cell size: $1.0-1.3 \times 1.5-4.7\mu$.
   (2) Polymorphism: Observed. This bacterium is cylindrical at an early stage of the cultivation and then turns to elliptic like an egg with the progress of the cultivation.
   (3) Motility: None.
   (4) Spores: Elliptic spores of $0.6-0.8 \times 1.2-1.5\mu$ in size are observed at the middle, subterminal or terminal site.
   (5) Gram staining: Positive.
   (6) Acid-fastness: None.
2. Growth in various media (cultured in each medium at 27° C. for one to seven days and observed in a conventional manner)
   (1) Bouillon agar plate culture
   The bacterium shows an excellent growth. It is in the form of a circle at first and then turns into an irregularly framed shape with multiplication. A colony thereof is glossy and milk white to pale yellow. No soluble pigment is observed.
   (2) Bouillon agar slant culture
   The growth surface is smooth at first and turns to wrinkled as the cultivation proceeds. It is opaque and adhesive. No pigment is formed.
   (3) Bouillon liquid culture
   No growth is observed on the surface. A slight turbidity is observed and a precipitate is observed at the bottom of the tube as the cultivation proceeds. No gas is evolved.
   (4) Bouillon gelatin stab culture
   Liquid layers are formed with the growth of the bacterium. No precipitate is observed.
   (5) Litmus milk culture
   The medium coagulates at 37° C. Peptonization is observed as the cultivation proceeds and the litmus turns to pale red.
3. Physiological properties
   (1) Reduction of nitrate: Negative.
   (2) Denitrification: Positive.
   (3) MR test: Quasi-positive.
   (4) VP test: negative.
   (5) Indole formation: Negative.
   (6) Hydrogen sulfide formation: Negative.
   (7) Hydrolysis of starch: Positive.
   (8) Utilization of citric acid: Positive.
   (9) Utilization of inorganic nitrogen sources:
   It does not seem to utilize inorganic nitrogen sources.
   (10) Formation of pigments
   King A, B: Both negative.
   (11) Urease: Negative.
   (12) Oxidase: Positive.
   (13) Catalase: Positive.
   (14) Growth range
   Temperature: 10° to 45° C. (cultured at various temperatures for 30 days).
   pH: 5 to 10.
   (15) Attitude for oxygen: Aerobic.
   (16) O-F test: Oxidation.
   (17) Formation of acids and gases from various sugars:
   Table 1 shows whether this bacterium produces acids and/or gases from each sugar.

TABLE 1

| No. | Sugars | Formation of acids | Formation of gases |
|---|---|---|---|
| 1 | L-arabinose | + | − |
| 2 | D-xylose | + | − |

TABLE 1-continued

| No. | Sugars | Formation of acids | Formation of gases |
|---|---|---|---|
| 3 | D-glucose | + | − |
| 4 | D-mannose | − | − |
| 5 | D-fructose | + | − |
| 6 | D-galactose | + | − |
| 7 | marutose | + | − |
| 8 | sucrose | + | − |
| 9 | lactose | + | − |
| 10 | trehalose | + | − |
| 11 | D-solbitol | − | − |
| 12 | D-mannitol | + | − |
| 13 | inositol | − | − |
| 14 | glycerin | + | − |
| 15 | starch | + | − |

(Used medium is a medium containing 0.5% agar in liquid medium.)

Based on these findings, this bacterium has been identified as a strain belonging to *Bacillus megaterium* by reference to Bergey's Manual of Determinative Bacteriology (the 8th ed.) and named *Bacillus magaterium* NK84-0218.

Similar to other strains belonging to the genus Bacillus, the *Bacillus megaterium* strain used in the present invention is labile in properties. Thus mutants thereof can be readily prepared by various artificial methods such as exposure to ultraviolet light or X-ray, or using chemical agents. Any mutants capable of producing the antibiotic NK84-0218, which is the object of the present invention, can be used in the present invention.

In order to produce the antibiotic NK84-0218 according to the present invention, the abovementioned strain is aerobically cultured in a medium containing nutrients which the microorganism can utilize. Well-known nutritional sources conventionally used in culturing bacteria can be employed. That is, carbon sources such as glucose, lactose, glycerol, sucrose, dextrin, galactose, organic acids and combinations thereof; and inorganic and organic nitrogen sources such as ammonium chloride, ammonium sulfate, urea, ammonium nitrate, sodium nitrate, peptone, meat extract, yeast extract, dry yeast, corn steep liquor, soybean powder, cotton seed meal, casamino acids, Bacto-Soytone (an enzymatic hydrolysis of soybean meal, mfd. by Difco Co., Ltd.), soluble vegetable protein, oatmeal and combinations thereof may be employed. Furthermore inorganic salts such as common salt, calcium carbonate, magnesium sulfate, copper sulfate, ferrous sulfate, zinc sulfate, manganese chloride and phosphates as well as organic compounds such as amino acids, vitamins and nucleic acids and inorganic compounds may be added if required.

Liquid culture, in particular submerged agitation culture, is the most suitable. It is preferable to culture the strain at 20° to 45° C. under a slightly acidic to slightly alkaline condition. This strain usually accumulates the aimed NK84-0218 in a liquid medium when cultured therein for one to four days. When the amount of the product reaches the maximum, the culture is ceased and the culturing broth obtained by filtering off the cells is purified to thereby isolate the aimed substance.

The amount of NK84-0218 accumulated in the culturing broth is determined by high performance liquid chromatography wherein a Nucleosil $_5C_{18}$ column ($4.6\phi \times 250$ mm) and a solvent (0.1M citrate buffer solution (pH 4.0)/acetonitrile/methanol=100:4:2) are employed at a flow rate of 0.8 ml/min at 21° C. and at 259 nm.

In order to isolate the antibiotic of the present invention, the culturing broth is purified in a manner conventionally used in isolating a metabolite of a microorganism from its culturing broth. NK84-0218 is soluble in water, methanol and dimethyl sulfoxide and hardly or not soluble in other conventional organic solvents such as propanol and acetone so that it is purified by a process conventionally employed to purify nucleoside antibiotics, i.e. adsorption/desorption with active carbon and ion exchange resins, column chromatography with the use of Avicel ® or Sephadex ® or a combination of these procedures. For example, the culturing broth is adjusted to a pH value of 3.5 to 6.5, preferably 4 to 4.5, adsorbed by powdery active carbon, washed with water and eluted with a 50% aqueous acetone and the active fraction thus obtained is concentrated and lyophilized to give a brown crude powder. Then this powder is dissolved in methanol and insoluble substances are removed. The soluble portion is dried, dissolved in water, adsorbed by an active carbon column, washed with water and subjected to acetone linear concentration gradient elution with water and 50% aqueous acetone. The obtained active fraction is concentrated and lyophilized. The pale brown powder containing NK84-0218 thus obtained is dissolved in a small amount of water and packed into an Avicel column. Then it is developed with an aqueous alcohol and eluted with increasing the water content stepwise. The active fractions thus obtained are combined, concentrated and lyophilized. Subsequently the obtained powder is dissolved in a small amount of water and packed into an SP Sephadex ® C-25(Na+) column previously equilibrated with 0.02M sodium chloride. The active fractions eluted with 0.02M sodium chloride are desalted on active carbon to give a colorless powder. The powder thus purified is treated with water or an aqueous alcohol to give NK84-0218 in the form of colorless needles. The titer during the cultivation is determined by plate cup assay with *Bacillus subtilis* PCI 219.

Alternately the substance of the present invention may be purified and isolated in the following manner. That is, the culturing filtrate is adjusted to a pH value of 4 to 4.5, adsorbed by a strongly acidic cation exchange resin, washed with water and eluted with diluted aqueous ammonia to give active fractions containing NK84-0218 which exhibits an antibacterial activity. These active fractions are combined, neutralized and passed through porous resin column. After washing with water and eluting with aqueous methanol, the obtained active fractions are concentrated in vacuo to give a crude powder containing NK84-0218. The obtained crude powder is dissolved in methanol and methanol is distilled off in vacuo from the soluble portion. The residue is passed through a weakly acidic cation exchange resin, washed with water and eluted with diluted aqueous ammonia. The obtained active fractions are combined and concentrated in vacuo to thereby remove the ammonia. Then it is allowed to stand in an icebox overnight to give crude crystals of NK84-0218. After recrystallizing from water, NK84-0218 is obtained in the form of colorless needles.

The NK84-0218 thus obtained has the following physicochemical properties.

(1) Appearance—Colorless needles.

| Elemental analysis (%) (as $C_{10}H_{13}O_3N_5.H_2O$) | | | |
|---|---|---|---|
| C | H | O | N |
| calculated: 44.60 | 5.62 | 23.77 | 26.01 |

-continued

| Elemental analysis (%) (as $C_{10}H_{13}O_3N_5 \cdot H_2O$) | | | |
|---|---|---|---|
| C | H | O | N |
| found: 44.75 | 5.58 | 23.65 | 25.98 |

(3) Molecular formula (molecular weight)—$C_{10}H_{13}O_3N_5$ (251.24).

(4) Melting point—197° C.

(5) Specific rotation—$[\alpha] = -44.3°$ (C 0.21, pyridine).

(6) Ultraviolet absorption spectrum

FIG. 1 shows ultraviolet absorption spectra of this substance.

Ultraviolet absorbances and molecular extinction coefficients in water, 0.1N hydrochloric acid and 0.1N sodium hydroxide are as follows, respectively:

$\lambda_{max}^{H2O}(\log \epsilon) = 259$ nm (4.10),
$\lambda_{max}^{0.1N\ HCl}(\log \epsilon) = 257$ nm (4.09),
$\lambda_{max}^{0.1N\ NaOH}(\log \epsilon) = 259$ nm (4.11).

(7) Infrared absorption spectrum

Figure 2:
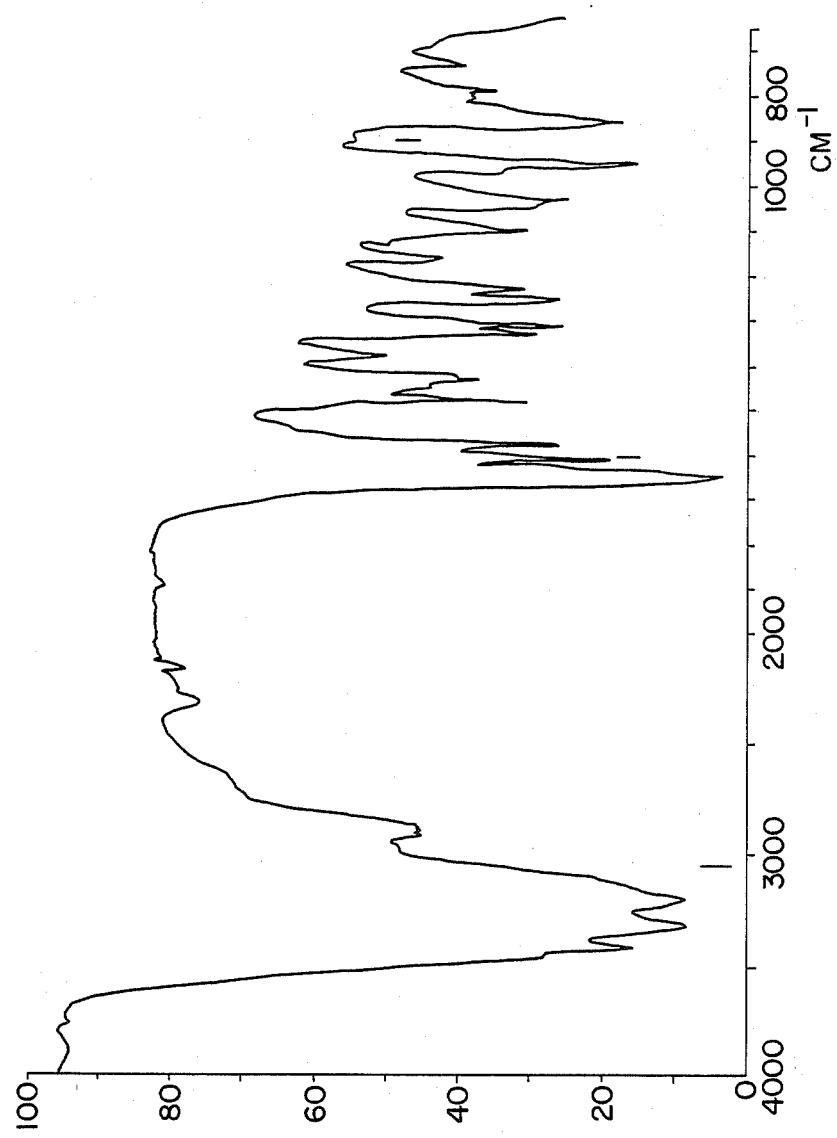
FIG. 2 shows an infrared absorption spectrum of NK84-0218 in the form of potassium bromide tablets.

FIG. 2 shows an infrared spectrum of this substance determined in the form of a potassium bromide tablets. Absorption maxima (wavelength; $cm^{-1}$) are as follows. 3470, 3420, 3325, 3200, 2925, 2890, 1655, 1615, 1587, 1565, 1548, 1510, 1490, 1455, 1440, 1430, 1388, 1370, 1333, 1317, 1300, 1257, 1230, 1200, 1165, 1130, 1100, 1045, 1030, 1010, 975, 955, 910, 860, 810, 795 and 743.

(8) Solubility in solvents

This substance is soluble in water, methanol, ethanol and dimethyl sulfoxide and hardly or not soluble in other organic solvents such as propanol, acetone, ethyl acetate, ether and benzene.

(9) Color reactions

Lydon-Smith's reaction and 10% sulfuric acid reaction: positive.

Ninhydrin reaction and Sakaguchi's reaction: negative.

(10) Rf values in thin layer chromatography

This substance shows Rf values of 0.51 and 0.48 in thin layer chromatography with the use of a silica gel thin layer (Kiesel gel 60 F254 0.25 nm; mfd. by Merck) and developed with n-butanol/acetic acid/water (4:1:2) and n-butanol/28% aqueous ammonia/water (10:0.5:1), respectively.

(11) $^1$H-nuclear magnetic reasonance spectrum

Figure 3:
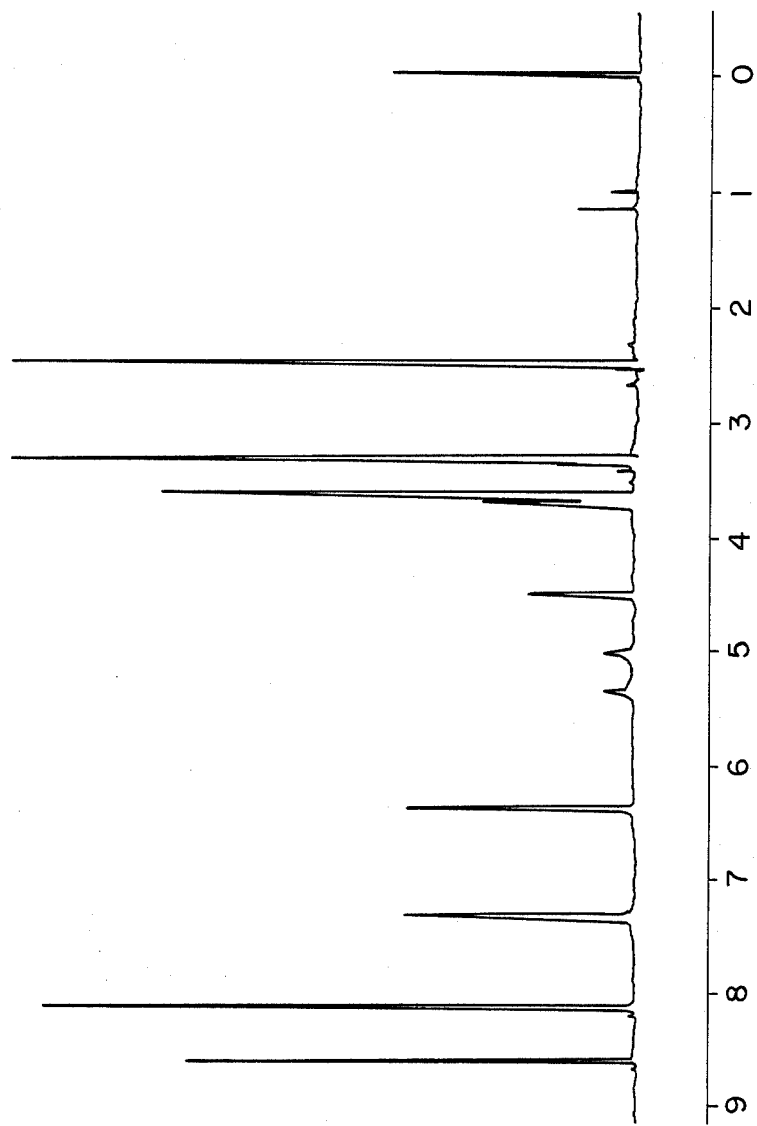
FIG. 3 shows a $^1$H-nuclear magnetic resonance spectrum of NK84-0218 determined with an apparatus at 400 MHz with the use of tetramethylsilane in deuterated dimethyl sulfoxide as an internal reference.

FIG. 3 shows a $^1$H-nuclear magnetic resonance spectrum determined by using tetramethylsilane in deuterated dimethyl sulfoxide as an internal reference.

(12) $^{13}$C-nuclear magnetic resonance spectrum

Chemical shifts ($\delta$ values) of a $^{13}$C-nuclear magnetic resonance spectrum determined by using dioxane ($\delta$67.4) in deuterated water as an internal reference are as follows:

156.4, 153.5, 149.3, 141.5, 119.4, 82.6, 80.1, 63.3, 59.9 and 45.4.

Based on these data as described above and that obtained by X-ray diffraction, the structure of NK84-0218 has been determined as described hereinbefore. Up to now, its absolute configuration has not been clarified.

As will be described hereinafter, the NK84-0218 of the present invention is expected to be available as pharmaceuticals such as an antibacterial agent, antiviral agent and an antineoplastic agent. It may be formulated into pharmaceuticals and administered in conventionally known manners. That is, it may be orally or parenterally (e.g., injection or rectoclysis) administered. It may be formulated into various forms such as injection, powder, granules, tablet and suppository.

Various pharmaceutically acceptable adjuvants such as carriers, stabilizers, antiseptics, soothing agents and emulsifiers may be used in formulating NK84-0218, if desired, so far as they exhibit no adverse effects.

The content of NK84-0218 in formulation can be varied in a wide range. Generally, a drug comprises 0.01 to 100% by weight, preferably 0.1 to 70% by weight, of NK84-0218 and the remainder being adjuvants such as a carrier conventionally used in the art.

The dose of NK84-0218 varies depending on symptoms and other factors. Generally 0.01 to 800 mg of NK84-0218 is administered to an adult patient in a day. It is preferable to decrease the daily dose when the substance must be repetitively administered.

NK84-0218 is usually formulated in the form of a pharmaceutically acceptable salt such as hydrochloride of sulfate.

Now biological activities of the NK84-0218 of the present invention will be described.

1. Antibacterial spectrum

Table 2 shows an antibacterial spectrum of NK84-0218 determined by agar plate dilution method with the use of 0.5% peptone agar.

As shown in Table 2, NK84-0218 exhibits intense effects of inhibiting the growth of gram-positive bacteria such as *Staphylococcus aureus* FDA 209P, those belonging to the genus Bacillus including *B. subtilis* PCI 219 and *B. cereus* IAM 1072 and *Micrococcus flavus* ATCC 10240 but no effect on gram-negative bacteria.

TABLE 2

| Tested bacterium | Minimum inhibitory concentration (μg/ml) |
|---|---|
| *Staphylococcus aureus* EDA 209P | <0.1 |
| *Bacillus subtilis* PCI 219 | <0.1 |
| *Bacillus subitilis* ATCC 6633 | <0.1 |
| *Bacillus cereus* IAM 1072 | <0.1 |
| *Bacillus polymyxa* IAM 1210 | <0.1 |
| *Bacillus megaterium* ATCC 14945 | 1.56 |
| *Bacillus licheniformis* IFO 12107 | 6.25 |
| *Micrococcus flavus* ATCC 10240 | 6.25 |
| *Micrococcus luteus* ATCC 9341 | 3.12 |
| *Escherichia coli* NIHJ | >100 |
| *Escherichia coli* K-12 | >100 |
| *Klebsiella pneumoniae* PCI 602 | >100 |
| *Proteus morganii* IFO 3168 | >100 |
| *Proteus vulgaris* IFO 3045 | >100 |
| *Proteus mirabilis* IFO 3849 | >100 |
| *Pseudomonas aernginosa* IFO 3445 | >100 |
| *Salmonella typhi* 901 (MS-1) | >100 |
| *Salmonella paratyphi* 1015 (MS-1) | >100 |
| *Salmonella enteritidis* G14 (MS-1) | >100 |
| *Enterobacter aerogenes* ATCC 13048 (MS-1) | >100 |
| *Serratia marcescens* GM 6484 | >100 |
| *Candida albicans* NIH 3147 | >100 |
| *Mycobacterium smegmatis* ATCC 607 | >100 |

2. Anti-HeLa cell activity

Table 3 shows the result of an examination on anti-HeLa cell activity of NK84-0218.

TABLE 3

| Concentration (μg/ml) | Cells/plate* (× 10$^5$) | Inhibition ratio (%) | IC$_{50}$ (μg/ml) |
|---|---|---|---|
| 100 | 2.78 | 93.38 | |
| 25 | 13.47 | 10.21 | ca. 47.0 |
| 6.25 | 13.91 | 6.94 | |
| 1.56 | 14.64 | 1.26 | |

TABLE 3-continued

| Concentration (μg/ml) | Cells/plate* (× 10⁵) | Inhibition ratio (%) | IC₅₀ (μg/ml) |
|---|---|---|---|
| 0.39 | 14.35 | 3.58 | |

*The number of cells 72 hours after the addition of NK84-0218.

As clearly shown in Table 3, the anti-HeLa cell activity (IC$_{50}$) of the NK84-0218 of the present invention is approximately 47.0 μg/ml.

(3) Antiviral activity

A medium containing a definite amount of NK84-0218 and herpes simplex virus-I (HSV-I) 5–10 TC ID$_{50}$ are added onto a single layer of vero cells in a microplate having 96 wells and cultured in a 5% by volume carbon dioxide incubator at 37° C. for 96 to 120 hours. Then the activiral activity of the test substance is determined by microscopically observing the cytopathic effect (CPE) of the HSV-I on the Vero cells.

Table 4 shows the result.

TABLE 4

| Concentration (μg/well) | Inhibition ratio (%) |
|---|---|
| 10 | 100 |
| 5 | 78 |
| 2.5 | 22 |
| 1.25 | 11 |
| 0.62 | 0 |
| 0 | 0 |

The inhibition is taken as effective when no CPE is observed in a well. For example, when CPE is observed in one well among ten at the same concentration, the inhibition ratio is 90%.

As shown in Table 4, the NK84-0218 of the present invention exhibits an antiviral activity.

The acute toxicity (LD$_{50}$) of NK84-0218 on mice is 100 mg/kg (i.v.) or above which is lower than those of various known nucleoside antibiotics.

These results as described above indicate that the NK84-0218 of the present invention may be expected as a novel pharmaceutical such as a novel antiviral agent, a novel antibacterial agent and a novel antineoplastic agent of a novel mechanism since it exerts an antiviral activity, an antineoplastic activity and an antibacterial activity on gram-positive bacteria such as *Streptococcus aureus* and *Bacillus subtilis* and is significantly different from conventional nucleoside antibiotics in its chemical structure.

To further illustrate the present invention, and not by way of limitation, the following Examples will be given.

EXAMPLE 1

100 ml of a seed medium (pH 7.2) comprising 2% of soluble starch, 0.5% of glucose, 0.5% of peptone, 0.5% of yeast extract, 0.05% of dipotassium phosphate, 0.05% of magnesium sulfate and 0.5% of soybean powder was pipetted into a Sakaguchi's reciprocating shake flask of 500 ml in volume and sterilized in an autoclave at 120° C. for 20 min. A platinum loopful of NK84-0218 strain (FERM BP-919) slant culture was inoculated thereto and cultured at 28° C. under shaking at 130 rpm for one day. Separately, 100 ml of a production medium (pH 7.4) comprising 2% of galactose, 2% of dextrin, 1.0% of Bacto-Soytone (mfd. by Difco Co., Ltd.), 0.5% of corn steep liquor (mfd. by Ajinomoto Co., Inc.), 0.2% of ammonium sulfate and 0.2% of calcium carbonate was pipetted into a rotary shake Erlenmeyer flask of 500 ml in volume and sterilized in an autoclave at 120° C. for 20 min. 2 ml of the above culturing broth was transplanted thereto and cultured therein at 27° C. under shaking at 192 rpm for four days. The culturing broth was filtered at pH 6.9 to give 18 L of a filtrate. (The titer was determined by peptone agar plate cup method with the use of *Bacillus subtilis* PCI 219 as a test organism and the culturing filtrate was referred to as 1 U/ml). The filtrate was passed through a column of active carbon for chromatography (Mfd. by Wako Chemicals Co., Ltd.) to adsorb NK84-0218 thereby. After washing with water, it was subjected to acetone linear concentration gradient elution with 2400 ml portions of water and 50% aqueous acetone. Active fractions were combined, concentrated in vacuo and lyophilized to give 4.72 g (0.6 U/mg) of a crude dark brown powder. Then this powder was treated with methanol and insoluble matters were removed. The residual soluble portion was dried in vacuo to give 1.91 g (2.0 U/mg) of crude brown powder. This powder was dissolved in 47 ml of water and adsorbed by a column of 150 ml of active carbon. After washing with water, it was subjected to acetone linear concentration gradient elution with 300 ml portions of water and 50% aqueous acetone. Active fractions were combined, concentrated in vacuo and lyophilized to give 657 mg (3.9 U/mg) of a pale brown powder. Then this powder was dissolved in 2.8 ml of water, packed into a column of 600 ml of Avicel ® previously equilibrated with n-propanol/water (97.5:2.5) and eluted with 1200 ml of n-propanol/water (97.5:2.5), 1200 ml of n-propanol/water (95:5) and 1200 ml of n-propanol/water (90:10), successively. Active fractions were combined, concentrated in vacuo and lyophilized to give 55.5 mg (34.8 U /mg) of a pale yellow powder. Then this powder was dissolved in a very small amount of water, packed into a column of 460 ml of SP Sephadex ® C-25 (Na+) previously equilibrated with 0.02M sodium chloride and eluted with the above sodium chloride. Active fractions were combined and desalted on active carbon to give 11.2 g (135.3 U/mg) of a colorless powder. This powder was dissolved in 1.1 ml of water and allowed to stand overnight at room temperature to give 10.1 mg of NK84-0218 in the form of colorless needles.

EXAMPLE 2

100 ml of a seed medium (pH 7.2) comprising 2% of soluble starch, 0.5% of glucose, 0.5% of soybean powder (Prorich), 0.5% of peptone, 0.5% of yeast extract, 0.05% of dipotassium phosphate, 0.05% of magnesium sulfate and 0.2% of calcium carbonate was pipetted into a rotary shake Erlenmeyer flask of 500 ml in volume and sterilized in an autoclave at 120° C. for 20 min. A platinum loopful of *Bacillus megaterium* NK84-0218 (FERM BP-919) slant culture was inoculated thereto and cultured at 27° C. and 200 rpm for 18 hours. Separately, 800 ml of the above medium was pipetted into a rotary shake Erlenmeyer flask of 5000 ml in volume and sterilized in an autoclave at 120° C. for 20 min. 10 ml of the above culturing broth was transplanted thereto and cultured therein under the same condition as described above for additional 18 hours. Further separately, 140 L of a production medium (pH 6.0) comprising 2.0% of soluble starch, 1.5% of soybean powder (Prorich; mfd. by Ajinomoto Co., Inc.), 0.3% of potassumprimary phosphate, 0.2% of sodium secondary phosphate, 0.0002% of cobalt chloride, 0.0002% of ferrous sulfate and 0.05% of magnesium sulfate was introduced into a stainless tank of 200 L in volume and subjected to pressure steam sterilization at 120° C. for 30 min. 2.4 L of the above culturing broth was transplanted thereto under a sterile condition and cultured therein at 37° C. under aerating at ⅔ VVM and agitating at 270 rpm for 43 hours. After the completion of the culture, the culturing broth was heated to 80° C. for five min, allowed to cool to room temperature and adjusted to a pH value of 3.8 with 10% sulfuric acid. Then 16 kg of a filter aid (Dicalite; mfd. by Dicalite Orient Co., Ltd.) was added thereto and cells were filtered off. 290 L of the filtrate (16.4 μg/ml) thus obtained was passed through a column of Dowex 50W×8 ® (H+, 19 L), washed with water and eluted with 200 L of 0.5 N NH₄OH/water. Active fractions containing NK84-0218 were adjusted to a pH value of 9.5 with 4N HCl/water, passed through a column of Diaion HP-20 ® (10 L), washed with water and eluted with 30 L of 40% aqueous methanol. Active fractions were combined, concentrated in vacuo and lyophilized to give 18.8 g (199 μg/ml) of crude NK84-0218 in the form of a dark brown powder. Then 380 ml of methanol was added to this powder and the mixture was stirred at room temperature for one to two hours. Then the methanol was removed in vacuo. To the residual portion soluble in methanol, water was added to prepare a 2% aqueous solution, which was subsequently passed through a column of Amberlite IRC-50 ® (H+, 500 ml), washed with water and eluted with 0.5N aqueous NH₄OH. Active fractions were concentrated in vacuo and allowed to stand in an icebox overnight to give 3.16 g (950 μg/ml) of NK84-0218 in the form of crude crystals. To this crude crystals, 130 ml of water was added and the mixture was heated to 40° to 45° C. to thereby dissolve the crystals. Then it was allowed to stand overnight in an icebox to give 2.85 g of NK84-0218 in the form of colorless needles. 1 mg of crystalline NK84-0218 was referred to as 1000 μg.

FORMULATION EXAMPLE 1

Distilled water was added to 30 parts by weight of the compound (I) to give a total amount of 2000 parts. After dissolving the compound, the solution was sterilized by filtering through a millipore filter of GS type. 2 g of the filtrate was introduced into a 10 ml vial and lyophilized therein to give a lyophilized injection containing 30 mg per vial of the hydrochloride of the compound (I).

FORMULATION EXAMPLE 2

50 parts by weight of the compound (I), 600 parts of lactose and 330 parts of crystalline cellulose were thoroughly mixed and the mixture was compacted with a Roller Compactor ®, ground and sifted to give granules passing through 16- to 60-mesh sieves.

FORMULATION EXAMPLE 3

30 parts by weight of the compound (I), 120 parts of crystalline lactose, 147 parts of crystalline cellulose and three parts of magnesium stearate were tabuleted in a V-type mixer to give tablets each weighing 300 mg.

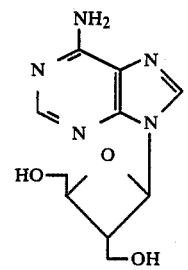

What is claimed is:

1. An antibiotic NK84-0218 of the formula: